United States Patent [19]

Hooper et al.

[11] Patent Number: 5,569,364

[45] Date of Patent: Oct. 29, 1996

[54] SEPARATION MEDIA FOR ELECTROPHORESIS

[75] Inventors: Herbert H. Hooper, Belmont; Stephen Pacetti, Sunnyvale; David S. Soane, Piedmont, all of Calif.; Young C. Bae, Seoul, Rep. of Korea

[73] Assignee: Soane Biosciences, Inc., Hayward, Calif.

[21] Appl. No.: 241,048

[22] Filed: May 10, 1994

Related U.S. Application Data

[63] Continuation-in-part of Ser. No. 971,956, Nov. 5, 1992, abandoned.

[51] Int. Cl.⁶ .................................................. C25B 9/00
[52] U.S. Cl. .................. 204/455; 204/462; 204/466; 204/468; 204/605; 204/613; 204/616; 252/315.1; 526/303.1; 526/306; 524/555
[58] Field of Search ............................ 204/182.8, 299 R; 252/315.1; 526/303.1, 306; 524/555

[56] References Cited

U.S. PATENT DOCUMENTS

| | | | |
|---|---|---|---|
| 4,732,930 | 3/1988 | Tanaka et al. | 524/742 |
| 4,863,613 | 9/1989 | Johnson et al. | 210/670 |
| 5,019,232 | 5/1991 | Wilson et al. | 204/182.8 |
| 5,100,933 | 3/1992 | Tanaka et al. | 523/300 |
| 5,135,627 | 8/1992 | Soane | 204/182.8 |
| 5,225,062 | 7/1993 | Yoshioka et al. | 204/299 R |
| 5,238,545 | 8/1993 | Yoshioka et al. | 204/182.8 |
| 5,242,491 | 9/1993 | Mamada et al. | 106/241 |

FOREIGN PATENT DOCUMENTS

| | | |
|---|---|---|
| 0501301A2 | 2/1992 | European Pat. Off. . |
| 9007978 | 7/1990 | WIPO . |
| 91/11709 | 8/1991 | WIPO . |

Primary Examiner—John Niebling
Assistant Examiner—C. Delacroix-Muirheid
Attorney, Agent, or Firm—Bertram I. Rowland, Ph.D.

[57] ABSTRACT

Separation media for electrophoresis, and methods of filling and flushing of electrophoretic devices such as capillaries are described. By preparing submicron to above-micron sized cross-linked gel particles and using gel swelling equilibrium concepts, such devices can be easily filled and flushed. Gel particles can be prepared by inverse suspension, precipitation and suspension polymerization. These particles can be swollen and collapsed by small changes in temperature, pH, and ionic strength of solvent. Other approaches involve the formation of reversible cross-links by use of polyelectrolyte complexes, chelating agents or copolymers of hydrophobic and hydrophilic repeat units. Finally, reversibly solubilized systems may be used to change the viscosity of the media.

24 Claims, 13 Drawing Sheets

30°C
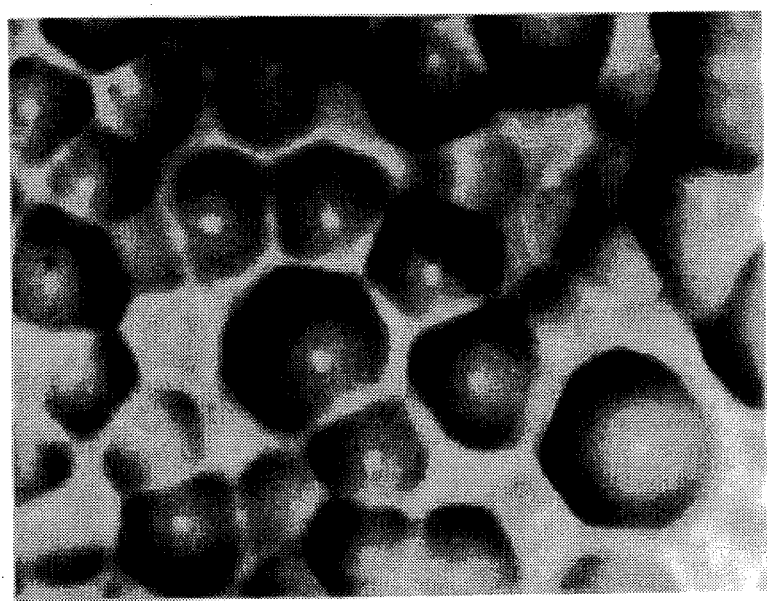
FIG. 8a
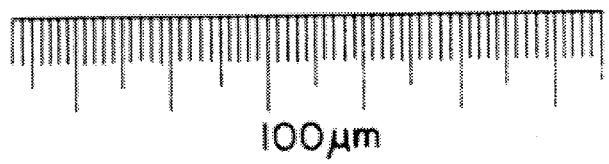
100μm
35°C
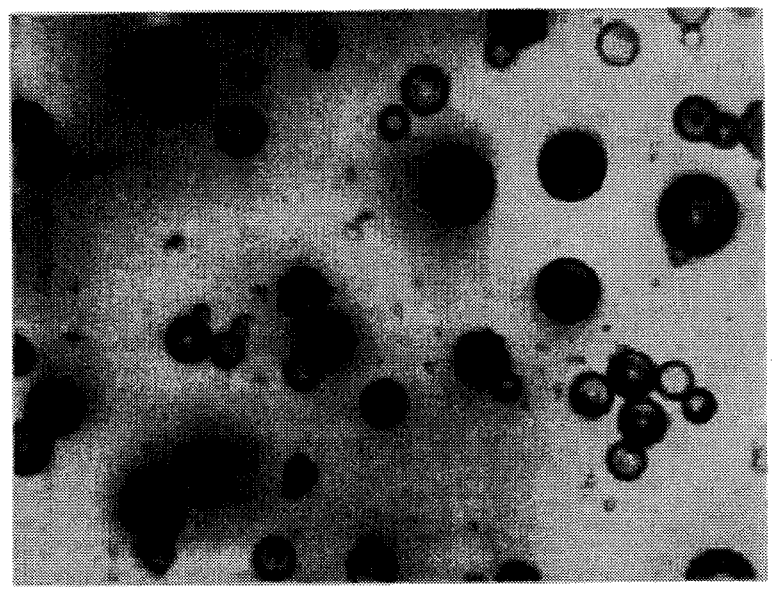
FIG. 8b
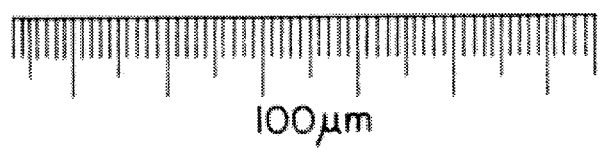
100μm

SEPARATION MEDIA FOR ELECTROPHORESIS

This application is a continuation-in-part application of U.S. Ser. No. 07/971,956, filed Nov. 5, 1992, now abandoned.

BACKGROUND OF THE INVENTION

This invention relates to the field of electrophoresis, more specifically, to a sieving medium for electrophoretic separation of biopolymers.

Electrophoresis is conducted in free solution or within a support medium which serves to minimize convection and diffusion, and in many cases to effect molecular sieving (see Andrews, Electrophoresis, 2nd Edition, Clarendon Press, Oxford, 1986). Cellulose acetate and paper are examples of electrophoresis matrices which do not affect separation, but serve primarily as anti-convective supports. Polyacrylamide and agarose gels have been used because they not only minimize convection and diffusion, but also act as molecular sieving matrices to molecules of a size comparable to that of the gel pores.

Polyacrylamide gels are typically prepared by free-radical polymerization of acrylamide in the presence of a crosslinking monomer, typically N,N'-methylene bisacrylamide. Agarose gels are prepared by dissolving agarose in a buffer solution at high temperature (70°–96° C., depending on the grade of agarose), and then allowing the solution to cool whereby an elastic gel is formed. Other forms of media have been described.

Numerous alternative acrylamide monomers and crosslinkers have been proposed with the objective of improving some aspect of gel performance, but leaving the basic procedure of gel preparation unaltered. (See general review by Righetti et al, J. Chromatography, 638, 165 (1993)). U.S. Pat. No. 5,055,517 to Shorr et al. discloses gels formed by polymerizing one or more acrylamide monomers, including various N-substituted acrylamide derivatives, with crosslinkers based on ethylene glycol dimethacrylate or poly(ethylene glycol) dimethacrylate. Mori et al in U.S. Pat. No. 5,164,057 describe electrophoresis media comprising at least one water-insolubilized temperature-responsive polymeric compound having an LCST. Mori et al describe conventional methods for rendering the matrix water-insolubilized, such as casting a crosslinked, macroscopic gel slab.

Radola et al, Biochim Biophys. Acta, 386, 181 (1974) describe isoelectric focusing in a flat bed of granulated, hydrophilic gel beads, such as dextran or polyacrylamide. In this method, a slurry of the granulated gel is prepared with excess water so that the slurry viscosity is low enough to allow it to be poured into a flat tray. After pouring, the excess water must be removed prior to conducting the separation. This is done either by evaporation or by transferring water into an absorbing material from the ends of the tray. The requirement of drying the bed after pouring adds significant time to the preparation, and is a source of inconsistent and poor separations due to insufficient or excess removal of solution after pouring. In addition, granulated beds have not been used for electrophoretic separations requiring molecular sieving, and electrophoretic migration is believed to occur in the interstices remaining between the granular particles of such conventional beds.

Native agarose is used but typically not at concentrations greater than 5% due the high viscosity of such solutions and the corresponding difficulty of pouring. Various agarose derivatives have been disclosed which have a finer pore structure, and therefore higher sieving power for small molecules, than native agarose. An example is hydroxyethylated agarose, described by Guiseley in U.S. Pat. No. 3,956,273. Nochumson et al (U.S. Pat. No. 5,143,646) describe small-pore resolving agarose gel blends comprising at least one depolymerized agarose.

Peacock and Dingman, Biochemistry, 7(21)668 (1968) disclose the preparation and use of agarose-acrylamide composite gels for electrophoresis. Polyacrylamide gels of very low concentration, which may be desirable to fractionate large molecules, do not have sufficient strength for handling. By polymerizing the acrylamide and crosslinker in the presence of agarose (which can be gelled before or after polymerizing the acrylamide), a composite matrix is created whereby the agarose provides structural support and the polyacrylamide acts as the primary sieving matrix. Agarose combined with prepolymerized, uncrosslinked polyacrylamide has also been suggested as an electrophoresis medium (Bode, Analytical Biochemistry, 83,204, 1977). However, this approach has disadvantages including the increased viscosity at the pouring temperature due to the presence of the linear polyacrylamide, and the potential for extraction of the unbound, water-soluble polymer during electrophoresis (particularly during submerged gel electrophoresis.)

As an alternative to covalently crosslinked gels, solutions of uncrosslinked, entangled polymers, such as polyethylene glycol, polyacrylamide, dextran, polyethylene oxide, methylcellulose, hydroxypropylmethylcellulose, and hydroxyethylcellulose have been employed as electrophoresis media (Bode, FEBS Lett., 65, 56, 1976; Tietz et al, Electrophoresis, 7, 217, 1986; Grossman and Soane, Biopolymers, 31, 1221, 1991; P. D. Grossman and D. S. Soane, J. Chromatography, 559, 257 (1991); M. J. Bode, FEBS Lett., 65, 56 (1991); M. Zhu, D. L. Hansen, S. Burd and F. Gannon, J. chroniatography, 480, 311 (1989); A. M. Chin and J. C. Colburn, Am. Biotech. Lab., 7, 16 (1989); D. Tietz, M. M. Gottlieb, J. S. Fawcett and A. Chrambach, Electrophoresis, 7, 217 (1986)). An advantage of this approach is that the medium can be injected into and flushed from a separation channel, such as a micro-capillary. Shortcomings of this approach include lower resolution than typically observed for non-viscous, crosslinked polyacrylamide matrices, and the often high solution viscosities, required. Osterhoudt et al (U.S. Pat. No. 5,149,419) describe preformed, water-soluble, acrylamide based copolymers comprising a minor proportion of a comonomer containing a crosslinking site. This crosslinking site is used to convert the polymer solution into a crosslinked electrophoresis network in situ by a reaction that does not involve free-radical addition. The crosslinking reaction described be Osterhoudt et al is not believed to be reversible, i.e., the gel network is apparently not reconvertible to a polymer solution.

The present invention is based on the discovery of an induced, and reversible, viscosity change, which changes the sieving characteristics of a polymer matrix. It is well known that the solubility of polymers in aqueous solution depends on several solution conditions including temperature, pH, ionic strength, the specific ions present in solution, and the presence and concentration of other molecular components in solution including other polymers, cosolvents, surfactants, etc. It was disclosed, for example, by Heskins and Guillet (J. Macromol. Sci.—Chem., A2 (8), 1441, 1968) that aqueous solutions of poly(N-isopropylacrylamide) exhibit a lower critical solution temperature (LCST), i.e. that aqueous solutions of this polymer phase separate at temperatures above the LCST. Taylor and Cerankowski (J. Polym. Sci.,

*Polym. Chem. Ed.,* 13, 2551, 1975) discuss numerous polymers that exhibit LCST behavior in aqueous solutions, and they demonstrate the change in swelling of a polymer film in solution that occurs at the LCST.

It is generally recognized that if a polymer exhibits an LCST in aqueous solution, then a crosslinked network of this polymer solvated in the same solution will undergo a significant (i.e., greater than 50%) increase in swelling, or volume upon a temperature decrease from above to below the LCST. This has been demonstrated for poly(N-isopropylacrylamide) (Hirokawa and Tanaka, *J. Chem. Phys.,* 81, 6379, 1984) and for poly(N,N'-diethylacrylamide) (Ilavsky et al, *Polym. Bull.,* 7, 107, 1982).

It is further recognized that any number of solution variables (e.g. pH, ionic strength, cosolvent concentration) which affect the solubility of a polymer in solution will also affect the solution swelling characteristics of a crosslinked gel composed primarily of the polymer. For example, the solubility of uncrosslinked polyacrylamide in solutions of acetone and water is known to decrease as the concentration of acetone is increased, and crosslinked polyacrylamide gel is known to exhibit a significant decrease in swelling in solutions of acetone and water as the acetone concentration is increased.

The swelling and contraction of polyacrylamide gel slabs in aqueous solutions due to temperature, various solutes and salts was investigated by Boyde (*J. Chrom.,* 124, 219 1976). Polyacrylamide is highly soluble in water and does not exhibit an LCST. Thus, while the swelling of polyacrylamide gel slabs in water was shown by Boyde to vary up to 40% with temperature, large (i.e., greater than 50 or 100%) changes in gel volume were not observed in response to temperature changes.

Tanaka et al (U.S. Pat. No. 5,100,933) disclose a method of causing a discontinuous volume change in a gel in response to changes in metal ion concentration, whereby the gel is an ionized, crosslinked polyacrylamide. In U.S. Pat. No. 4,732,930, Tanaka et al disclose ionic isopropylacrylmide gels which exhibit volume changes in response to solvent composition, temperature, pH or ion composition.

The present invention is useful for electrophoresis, in general, and, in particular, for improving capillary electrophoresis (CE), which has found widespread applications in analytical and biomedical research. The scope and sophistication of CE are rapidly increasing. CE can perform analytical separations that are often substantially better than those using established chromatographic methods such as high-performance liquid chromatography (HPLC). The separation modes of the conventional electrophoretic methods are slow, labor-intensive, prone to relatively poor reproducibility and have limited quantitative capability. Furthermore, it has been difficult to fully automate the process. The major advantages of capillary electrophoresis are that it can be fully automated, offers high resolution, and can quantitate minute amounts of samples, as reviewed by N. A. Guzman, L. Hernandez and S. Terabe, *Analytical Biotechnology,* Chapter 1, ed. by C. Horvath and J. G. Nikelly. ACS symposium series, ACS, Washington, DC (1990). These capabilities lie far beyond those of traditional electrophoretic methods.

CE has recently been used in the analysis of an extremely wide variety of molecules, including organic and inorganic anions and cations, drugs, dyes and their precursors, vitamins, carbohydrates, catecholamines, amino acids, proteins and peptides, nucleic acids, nucleotides, DNA and oligonucleotides. In comparison with gas chromatography, supercritical fluid chromatography, and liquid chromatography, CE is the best separation technique from the point of view of molecular weight range of applicability. It is possible to separate in the same column species ranging in size from free amino acids to large proteins associated with complex molecular matrices.

From the detection point of view, HPLC provides better concentration sensitivity and CE provides better mass sensitivity. However, initial attempts to resolve complex mixtures of biological macromolecules in open CE columns were disappointing. The complex protein macromolecules present a serious problem when using untreated fused-silica capillaries due to the adsorption of many proteins onto the walls of the capillary. With oligonucleotides, the unfavorable mass-to-charge ratio tends to cause comigration of larger mixture components.

A highly advantageous solution to these difficulties was the development of gel-filled capillaries. Remarkably high separation efficiency has been obtained by gel-filled CE. To accomplish size selection in electrophoretic separation of mixtures of nucleic acids and SDS-denatured proteins, a cross-linked gel matrix is employed. However, the routine preparation of homogeneous stress-free gels in capillaries is difficult due to polymerization induced shrinkage and appearance of bubbles inside the capillaries.

The resolving power of capillary electrophoresis (CE) using the prior art entangled polymer solutions as the separation media is not good for large analyte molecules, presumably as a result of the relevant time scales of the sieving polymers and analyte molecules. The residence time (or passage time) of analyte molecule in a mesh is controlled by the size and electrophoretic mobility of the analyte, mesh size of the network, and the imposed electric field strength. The life time of entanglement, i.e., mobility of strands forming the mesh, depends on network integrity, the length and concentration of macromolecules constituting the network. In order to achieve good resolution, the relaxation time of the entangled polymer solution should be orders of magnitude greater than the residence time of the analyte molecules.

Unfortunately, this condition does not necessarily hold in typical CE applications, as demonstrated in the examples separating DNA by CE using entangled polymer solutions, reported by T. Hino, *MS Thesis,* University of California, Berkeley (1991), demonstrating that the slow-mode relaxation time of polyacrylamide was $5.9 \times 10^4$ sec (T3%, 25° C.) for entangled solutions and $4.0 \times 10^{-3}$ sec (T3%, 25° C.) for cross-linked systems. The typical residence time of DNA can be estimated from the literature (P. D. Grossman and D. S. Soane, Biopolymers, 31, 1221 (1991); P. D. Grossman and D. S. Soane, *J. Chromatography,* 559, 257 (1991); J. Sudor, F. Foret and P. Bocek, *Electrophoresis,* 12, 1056 (1991)) by assuming the two extremes (Ogston and biased reptation)= Residence time between $$\left( \frac{\text{mesh size}}{(\text{electrophoretic velocity})_{Ogston}} \right)$$

and $$\left( \frac{\text{DNA contour length}}{(\text{electrophoretic velocity})_{reptation}} \right)$$

where subscript Ogston means that the migrating solute behaves as an undeformable particle (Ogston Model) and reptation under the influence of large electric fields, the solute becomes more elongated, and the motion mimics that of a snake threading its way through the network. The calculated residence time limits of DNA are as follows: $1.5 \times 10^{-5}$ to $1.8 \times 10^{-4}$ sec. for 30 base pairs and $1.5 \times 10^{-5}$ to $8.2 \times 10^{-4}$ sec. for 100 base pairs. The calculated residence times of 100 base pairs are extrapolated from 30 base pairs data based on a hydrodynamic diameter per base pair of 3.3 Å (K. S. Schmitz, *An Introduction to Dynamic Light Scattering by Macromolecules,* Academic Press, NY (1990); V. A. Branfield, Chapter 10, *Dynamic Light Scattering,* Plenum Press, NY (1985)). The results show clearly that the relaxation time of entangled polymer and residence time of DNA are very close. Therefore, sharp resolution cannot be expected for the high molecular weight of DNA using entangled polymers. The network imposing the sieving medium fails before the analyte moves through a mesh completely.

In summary, the conventional electrophoretic methods are slow, labor-intensive, with relatively poorly reproducibility and have limited quantitative capability. Furthermore, it is difficult to accomplish a fully automated operation. CE promises to offer a solution for those problems. However, choosing the sieving medium is difficult. Open CE columns adsorb many proteins onto the walls of the capillaries. A cross-linked gel filled CE is complicated by problems in the routine preparation of homogenous stress-free gels in capillaries due to polymerization induced shrinkage and appearance of bubbles inside the capillaries. Entangled polymer solutions in the capillaries exhibit poor resolution and reproducibility. All the above problems can also be found with slab gel electrophoresis as well as other electrophoretic configurations.

It is therefore an object of the present invention to provide an improved method and medium composition for separation of molecules, especially by capillary gel electrophoresis.

It is a further object of the present invention to provide a method and means to improve the resolution and reproducibility of entangled solutions, in combination with the ease of fill/flush.

It is another object of the present invention to provide a new class of separation media for CE and related electrophoretic technologies, including slab and annular configurations, as well as sequencers for DNA and protein, and methods of preparation and use thereof.

SUMMARY OF THE INVENTION

The present invention provides electrophoresis media in which a viscosity change can be induced such that the media can be poured or pumped into or out of the separation chamber or channel at the lower viscosity, and electrophoresis can be conducted at the higher viscosity. Further, the viscosity change is accompanied by a change in the sieving characteristics of the matrix, such that the higher viscosity state possesses superior sieving properties to the lower viscosity state. The viscosity change is reversible, so that, if desired the matrix can be recovered from the separation chamber or channel in the low viscosity state, and further analyzed, for example, by staining and visualization to determine the location of components of the sample on the media.

Methods of preparing sieving media and of filling and flushing of capillaries and other electrophoretic devices are provided which combine the advantages of gel filled and entangled-polymer-solution filled systems such as good resolution, ease of fill and flush, and reuse of the capillary or device. Three classes of sieving media are presented having these properties.

BRIEF DESCRIPTION OF THE DRAWINGS

FIG. 8A and 8B show magnified photographs of the microgel dispersion made according to Example 3 at 35° C. and at 30° C.

DETAILED DESCRIPTION OF THE INVENTION

Figure 1:
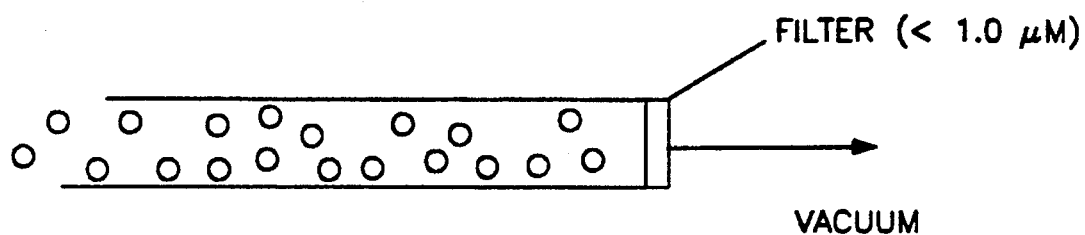
FIGS. 1A, 1B, and 1C are schematics of filling (FIG. 1A), swelling (FIG. 1B), and deswelling and flushing capillaries (FIG. 1C).
Figure 1:
Figure 1:
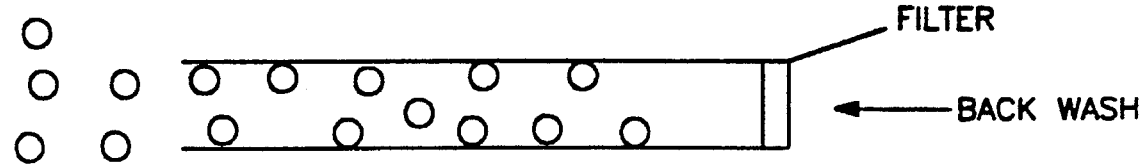

It has been discovered that a suspension or dispersion of crosslinked polymer particles in solution will exhibit a large (greater than 100%) change in viscosity in response to one or more solution variables (e.g., temperature, pH, solution composition) if the particles are comprised of a gel which exhibits a significant change (i.e., greater than 50% increase) in swelling characteristics in response to the same solution variable(s). It has further been discovered that certain of such suspensions or dispersions can be employed as separation media for electrophoresis at the higher viscosity state. It has also been discovered that uncrosslinked polymer can be delivered to a separation channel not only as a solution, but also as a dispersion or suspension of polymer particles. After delivering the dispersion or suspension of insoluble polymer particles to the separation channel, the solution conditions are changed such that the polymer becomes solubilized in the solution. This solubilization is accompanied by an increase in viscosity. Analogous to the situation observed with the crosslinked gel particles, the sieving properties of the higher-viscosity medium are superior to that of the low viscosity medium. It has also been discovered that uncrosslinked polymer solutions which exhibit reversible crosslinking can be employed as electrophoretic sieving media. Analogous to the crosslinked gel particles and the reversibly solubilizable polymer solutions, the reversible crosslinking is accompanied by a viscosity change, and the sieving properties of the solution are superior at the higher viscosity state.

All three classes of separation media disclosed herein exhibiting a viscosity change have been developed for use with capillary electrophoresis (CE) as well as conventional slab and other types of electrophoresis. The media is selected to have a low viscosity state for ease of filling and a high viscosity state that has good electrophoretic resolution.

The media may contain ionic and/or nonionic surfactants and water-soluble polymers, as appropriate for handling, attaining appropriate end point viscosities, and wetting.

The media is not only easy to use but in the case of the crosslinked systems achieves high resolution. For example, the relaxation time of polymer is orders of magnitude greater than the residence time of DNA. As a result, cross-linked systems lead to much better resolution than those of entangled polymer solutions.

REVERSIBLY SWELLING CROSSLINKED MICROGEL SYSTEMS

Sieving media are provided comprising a solution of particulate chemically-crosslinked microgel having a size distribution of particles no smaller than about 10 nm and no larger than about 2 mm, wherein the weight concentration of the microgel in the solution is between about 1% and 50%, and the solution can be reversibly converted between a low viscosity state and high viscosity state wherein the high viscosity state is at least 100% greater than the viscosity of the solution in the low viscosity state, and the changes between the high and low viscosity states can be affected by changing of temperature, pH, solvent concentration, ionic concentration or other property or combination of properties of the solution. The change from the low viscosity state to the high viscosity state is driven by an increase of the volume of the particles by at least about 50%. The cross-linked gel particles are prepared by suspension (polymerization) or precipitation polymerization. The gel particles formed by these methods can be as small as in the range of 300 Å–500 Å to as large as microns or tens to thousands of microns. Optimal range of the cross-linked microgel size depends on the gel swelling ratio and dimensions of the electrophoresis channel. The aqueous medium for the gel particles can be a buffered solution of various pH and ionic strength or pure deionized water depending on the specific application. For filling separation channels the optimal loading of gel particles in suspension may be determined by the viscosity of the suspension with gel particles and swelling/deswelling considerations. In one embodiment of the invention, the procedure for use includes the steps of 1) filling the electrophoresis channel, 2) swelling and running, and 3) deswelling particles and capillary flushing. In another embodiment of the invention, following step (2) the swollen particle network is removed from the electrophoretic device as an intact gel slab or tube and subjected to further manipulation. Handling of the swollen microgel network in this manner is rendered possible by incorporating a second gel-forming polymer, such as agarose, in the original suspension. The media may also be poured onto a surface to from a granular bed, wherein the polymer particles per se are the molecular sieves, as opposed to a conventional bed wherein particles are not sieves and the analytes pass through the interstices between the particles. Swelling of gel particles can be effected by a change of temperature, pH and ionic strength of solution, and vice-versa for deswelling.

Inverse Suspension Polymerization.

The term 'inverse' suspension polymerization is used to imply a heterogeneous polymerization system in which the monomer is readily soluble in water, but only sparingly soluble, if at all, in non-polar liquids. Thus, in the inverse suspension polymerization an aqueous solution of a hydrophilic monomer is dispersed in a continuous hydrophobic medium using a surface-active substance which promotes the formation of water-in-oil emulsions. The polymerization is then initiated with water-soluble initiators. Sorbitan monostearate is a water-in-oil emulsifier which is suitable for this application.

The inverse suspension polymerization is as follows. The suspensions are formed by dissolving the emulsifier in o-xylene or a suitable organic medium such as toluene and adding the aqueous monomer solution with stirring. The crude suspensions are homogenized to decrease the average droplet size and increase the emulsion stability. The suspensions are heated with stirring at 40° C. to 70° C. to effect polymerization. The time required for complete conversion varies from a few minutes to several hours. The particles formed by this method can be as small as 300 Å depending on the amount of surfactant added. To purify, the particles are centrifuged several times with deionized water.

Precipitation Polymerization.

For precipitation polymerization, one needs to know the phase diagram of polymer solutions. For example, the lower critical solution temperature (LCST) of poly-N-isopropylacrylamide poly(NIPAM) in an aqueous medium is about 32° C. Thus it will be precipitated if the polymerization temperature is above 32° C. during polymerization. Table 1 shows other similar systems such as polyNIPAM in aqueous medium whose LCSTs are known.

TABLE 1

| List of LCSTs of aqueous polymers | |
|---|---|
| Polymer and Copolymers | LCST (°C.) |
| poly (N-methylacrylamide) | 95 |
| poly (N-ethylacrylamide) | 80 |
| poly (N-n-butylacrylamide) | 25 |
| N-isopropylacrylamide - co-N-isopropylmethacrylamide | 23–40 |
| poly (N-n-propylacrylamide) | 16–19 |
| poly (N-n-propylmethacrylamide) | 22–29 |
| poly (N-isopropylacrylamide) | 32 |
| poly (N-isopropylmethacrylamide) | 40 |
| poly (N-ethylmethacrylamide) | 54–57 |
| poly (N-acroylpiperidine) | 4–6 |
| poly (N-methacroylpiperidine) | 18–42 |
| poly (N-pyrolichylmethacrylamide) | 53 |
| poly (N-piperidylmethylacrylamide) | 42 |
| poly (N,N'-diethylacrylamide) | 30–32 |

The method is generally as follows. Water soluble monomers are dissolved in water in a round bottom flask equipped with a condenser, a nitrogen inlet, and a stirrer. Nitrogen is bubbled into the solution and the temperature is controlled at 70° C. Potassium persulfate can be used as an initiator. The reaction is then continued for 24 hrs under mild stirring. The resulting microgels are centrifuged to separate them from the suspending medium. They are redispersed in water and then are centrifuged several times to increase purity. The size of the microgels can be as small as 500 Å or greater depending on polymerization temperature and stirring conditions, i.e., the faster the mixture is stirred, the smaller the microspheres.

The monomers that can be used in the above methods include N-adamentylacrylamide, N-benzylacrylamide, N-benzylmethacrylamide, N-cyclohexylacrylamide, N,N'-diethylacrylamide, dodecylmethacrylamide, N-isobornylacrylamide, N-methymethacrylamide, diacetone acrylamide, N-[3-(dimethylamino) propyl] acrylamide, methacrylamide, and (1-naphthyl methyl) methacrylamide. The following can be used as crosslinkers: N,N'-bis (1,2-ethylene) dimethacrylamide, N,N'-ethylenebisacrylamide, N,N'-hexamethyl bisacrylamide, N,N'-methylenebisacrylamide, methylenebismethacrylamide, N,N'-nonomethylenebisacrylamide, N,N'-octamethylenebisacrylamide, NN'-(isopropylidene) bisacrylamide, NN'-trimethylenebisacrylamide, piperazine diacrylamide, N,N'bisacrylylcystamine, and N,N'-diallyltartardiamide. Other monomers and crosslinkers are known to those skilled in the art and can be used in place of any of those listed above.

Loading of Capillaries.

After preparation the microgels can be injected, or drawn in by vacuum into capillaries, as shown in FIGS. 1A, 1B and 1C. Note that during injection the particles are in a collapsed state. Optimal range of the cross-linked microgel size depends on the gel swelling ratio and diameter of the capillaries. The diameter of the capillaries usually varies from 50 μ to 250 μ. From gel swelling equilibria data, one can predict the number density of microgels in aqueous medium. This aqueous medium can be a buffer solution or deionized water, depending on the specific particles in suspension for filling capillaries, which is determined by the viscosity of the suspension (with particles) and swelling/deswelling considerations.

Figure 2:
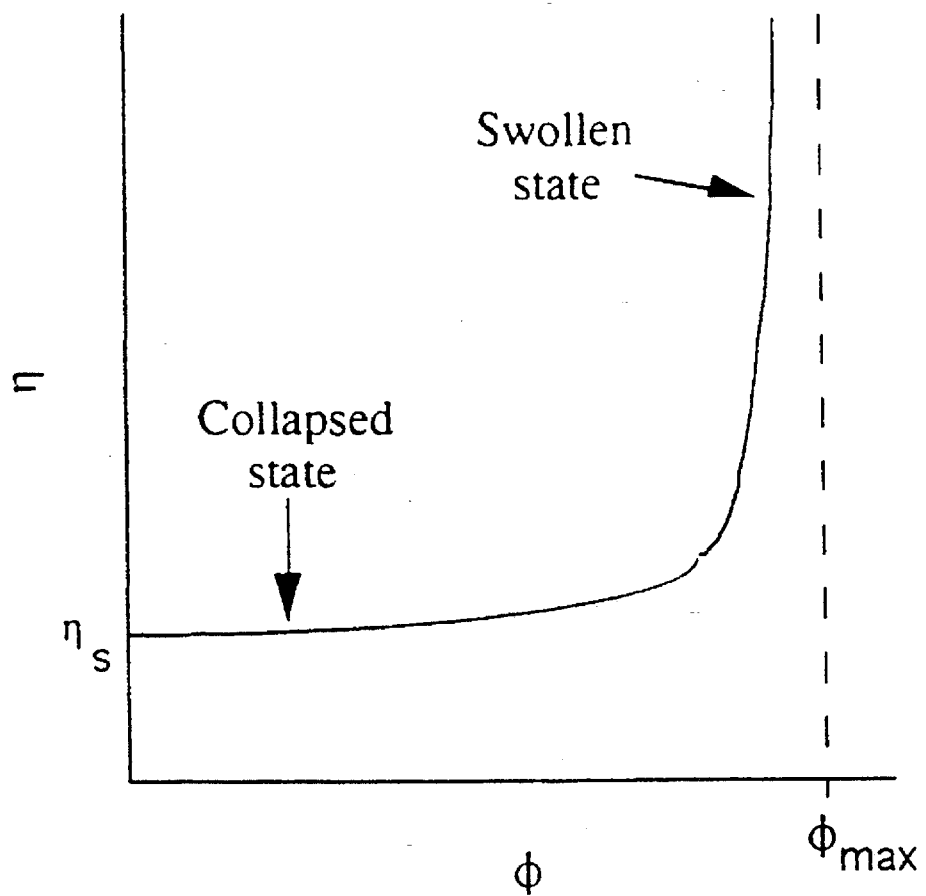
FIG. 2 is a graph of the viscosity of suspensions as a function of volume fraction of fillers.

FIG. 2 shows a typical viscosity curve of suspension with fillers. The viscosity can be expressed by $$\ln\left(\frac{\eta}{\eta_s}\right) = \frac{K_E \phi}{1 - \frac{\phi}{\phi_{max}}}, \quad \text{equation 8}$$

where $\eta$ is the viscosity of aggregate-filled suspension, $\phi$ the volume fraction of fillers, $\eta_s$ solvent viscosity, and $K_E$ is a geometric factor. If one assumes the particles are spherical, $K_E = 2.5$ (Einstein's equation).

Variation in Gel swelling at each stage of process.

At the first stage, the capillary filling stage, the temperature should be controlled at the above-the-discontinuous volume-change phase region, so that the particles are in a collapsed state. By knowing the swelling ratios of gels, the number density and size of particles can be determined. At the end of the capillary, one can put a filter whose pore size is less than the collapsed particles so that only the suspending liquid can pass through, as shown in FIG. 1A.

At the second stage, the swelling and running stage, the temperature should be raised above the discontinuous-volume-change-region so that the particles are swollen. As shown in FIG. 1B, the total particle volume is such that the particles deform against one another to become a continuous phase. As a result, the capillary is filled with particles only and contains minimal void space.

In the third stage, deswelling particles and capillary flushing, the temperature is changed to the temperature used in the capillary filling stage so that the particles collapse.

In one variation, the pore sizes of the particles may be changed during the running stage. Thus, the conditions may be set in the media and the analyte may be partially separated on the media. Then the conditions may be changed, for example, by swelling to increase the pore size, and more defined separations may be obtained by one or more separation steps.

Deswelling of gels can be accomplished by several methods other than changing temperature. Reversible swelling and contraction of ionic gels can be effected by changes of pH and ion compositions consistent with the essential role of ionization in phase transition. When the pH varies or salt ions are added to the solvent, the effective number of counterions varies, as does the ionic osmotic pressure. The higher the pH or ion concentration, the more the gel swells. Changes in the ionic composition can also induce a phase transition. The concentration needed for the transition differs by four orders of magnitude between monovalent NaCl and divalent $MgCl_2$. It is possible to use a combination of parameters synergistically to achieve deswelling. For example, one can change the temperature to a point at which the gel spheres shrink and then pass a buffer solution through low pH or low ion concentration by electrophoresis. Thus, the gel spheres shrink further, and can be easily flushed out of the separation device (capillary slab, or annular), as shown in FIG. 1C.

Figure 3:
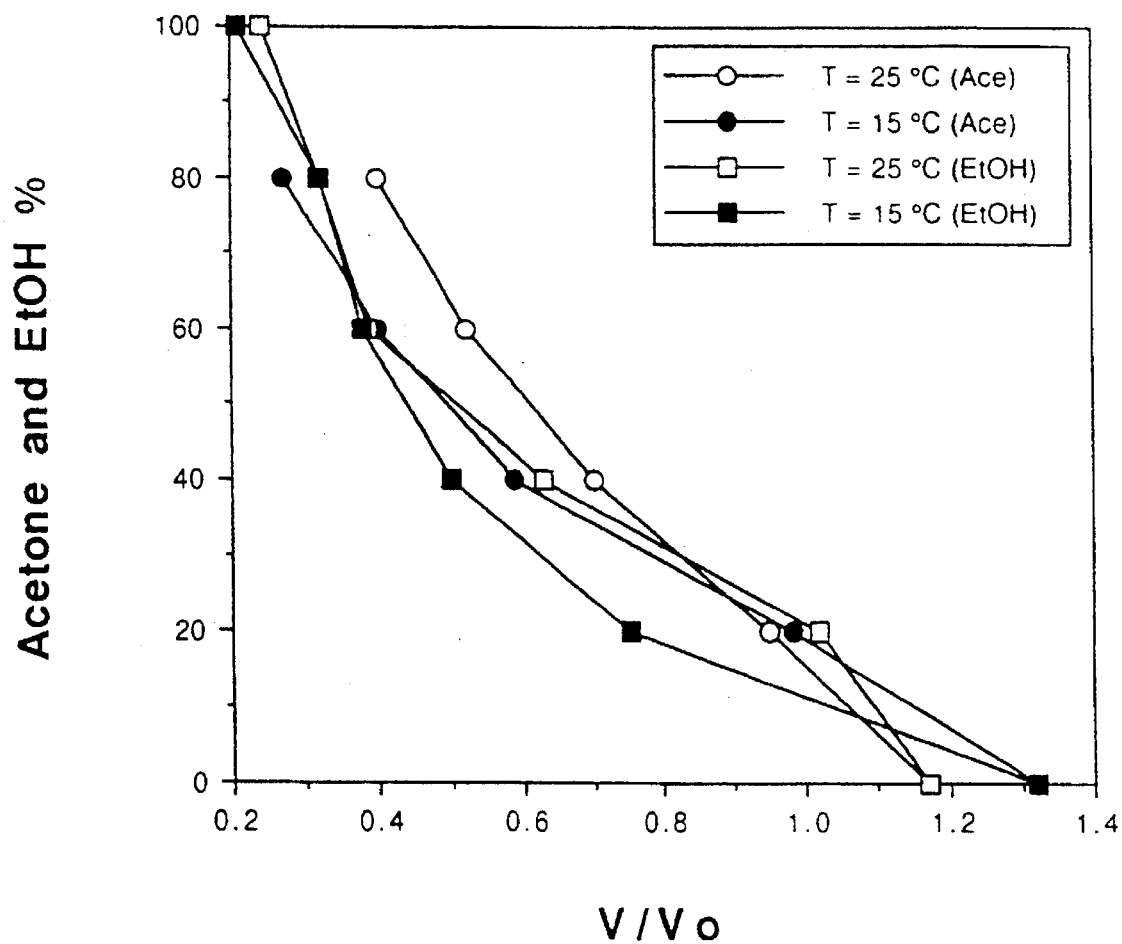
FIG. 3 is a graph of the gel swelling ratio ($V/V_o$) of a polyacrylamide gel slab with respect to the volume fraction of acetone and ethanol at different temperatures: open circle, 25° C. Acetone; closed circle, 15° C. Acetone; open square, ethanol; and closed square, 15° C. ethanol.

Alternatively, as shown in FIG. 3, with the acrylamide monomers referenced above, a ketone such as acetone or low alcohol such as methanol or ethanol is injected into the capillary so the particles are collapsed to a minimum for easy flushing.

REVERSIBLY CROSSLINKABLE SYSTEMS

There are at least three different approaches in reversibly crosslinkable systems. First, by copolymerizing hydrophilic and hydrophobic monomers into blocky structures, the hydrophobic region can be physically bonded and released by changing temperature and ionic strength of the buffer solution. Second, exchanging monovalent ions for divalent ions by electrophoresis can make a sieving medium which contains conjugate functional groups cross-link or dissociate. Third, by adding a chelating agent a crosslink can be formed between neutral functional groups such as hydroxyl or amino groups. The crosslink is reversible via addition of strong acid or oxidizer.

Figure 4A:
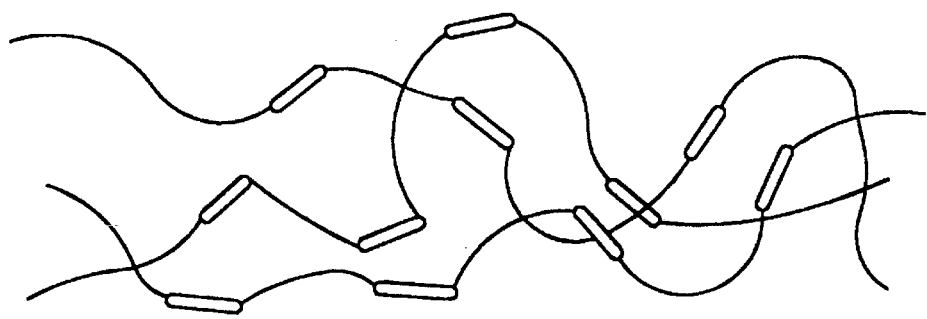
FIGS. 4A and 4B are schematics illustrating physically cross-linked systems. Thin lines are hydrophilic polymers and thick lines are hydrophobic polymers. The shaded areas represent physically bonded regions, via the hydrophobic salting out phenomenon.
Figure 4B:
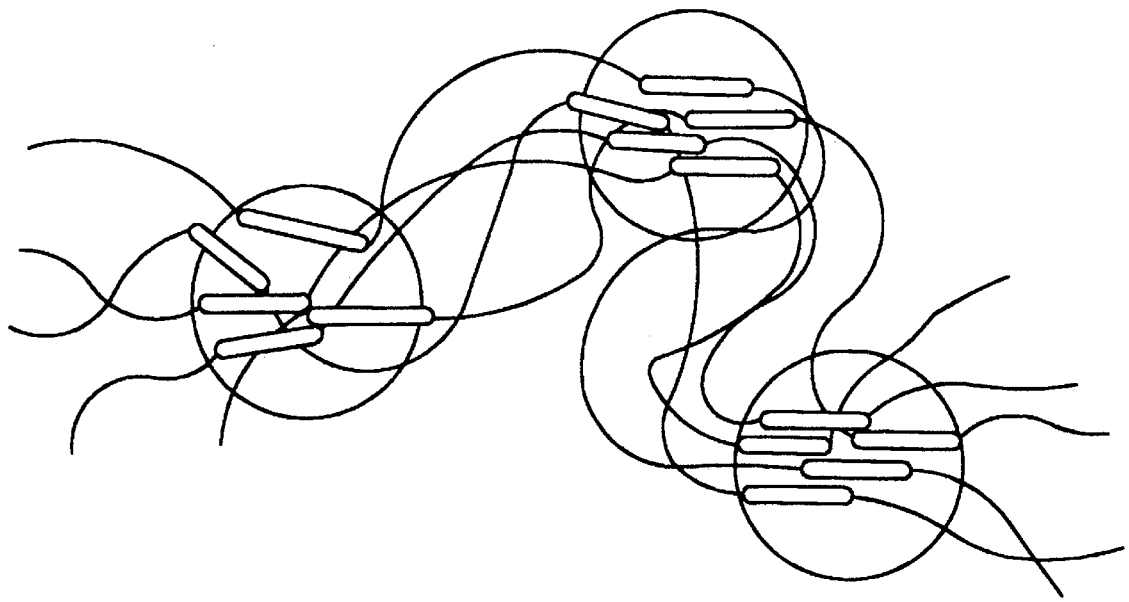

FIG. 4 is a schematic illustration of one reversibly crosslinkable system. In this Figure, thin solid lines denote hydrophilic regions and thick solid lines represent hydrophobic region. Under normal conditions, the copolymers are linear (see FIG. 4A), however, by changing the solvent conditions, such as temperature and ionic strength (or pH), the hydrophobic regions may coalesce and the copolymer behave like a cross-linked system, as shown in FIG. 4B. In this way, the capillary can be filled at a certain temperature, ionic strength and pH at which the polymer molecules are separate and can easily flow. Then the system can be reversibly cross-linked by a change of temperature and/or ionic strength and pH. After the analysis, the capillary can be easily flushed by changing these conditions back to the conditions at which the capillary was filled.

Figure 5A:
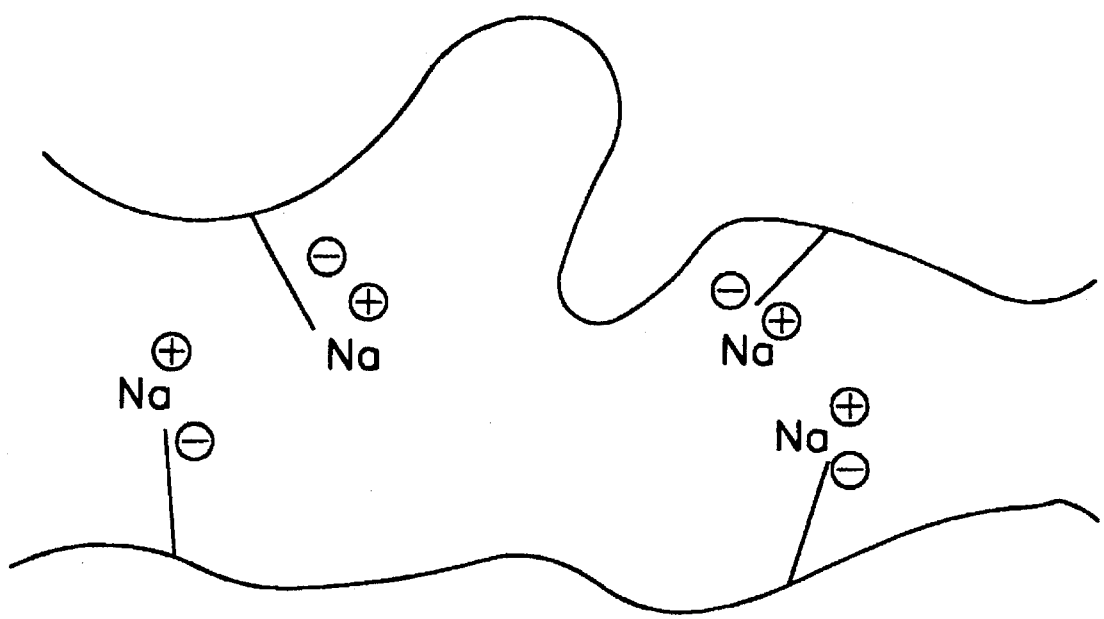
FIGS. 5A and 5B are schematics of ionic association, forming physical cross-links: 5A, dissociated state, 5B, associated state.
Figure 5B:
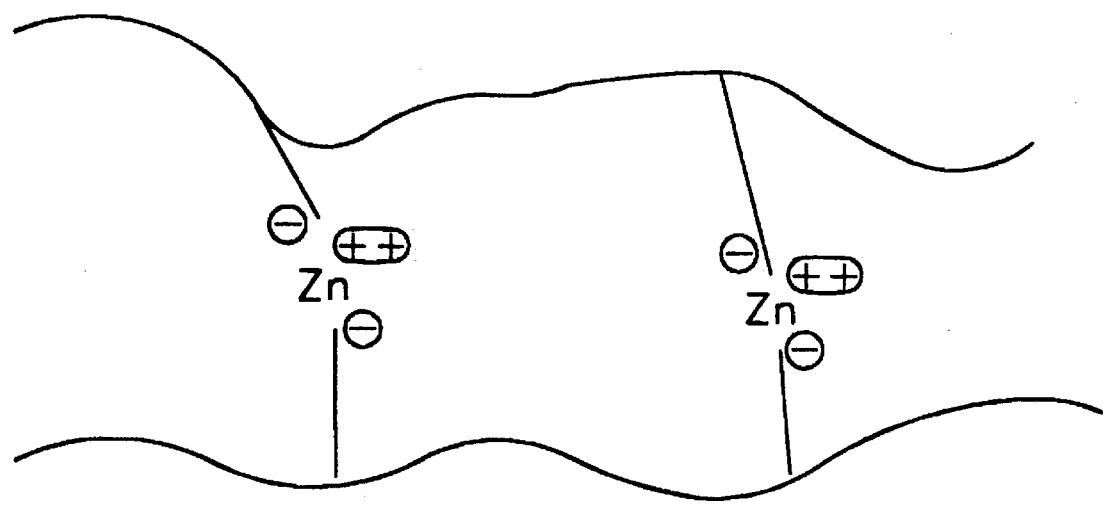

The second method for a reversibly crosslinkable system utilizes exchange of monovalent ions and divalent ions, for example, by electrophoresis of buffers, to make a sieving medium containing conjugate functional groups cross-link or dissociate. FIGS. 5A and 5B illustrate this process. In FIG. 5A, the polymers are not cross-linked. In FIG. 5B, a buffer containing zinc divalent ions has been added, displacing the sodium salts and crosslinking the polymers.

Figure 5C:
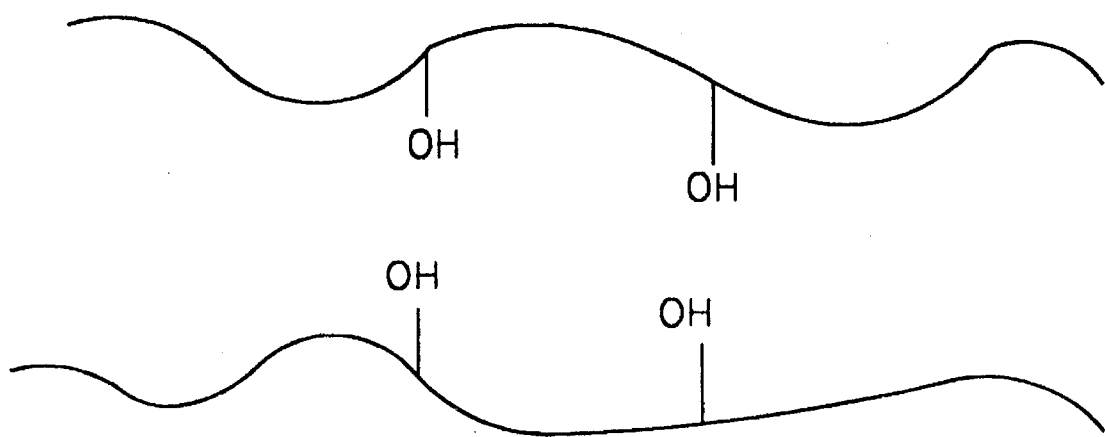
FIGS. 5C and 5D are schematics of chelated association, forming physical cross-links: 5C, dissociated state; 5D associated state, using Ti ion as an example.
Figure 5D:
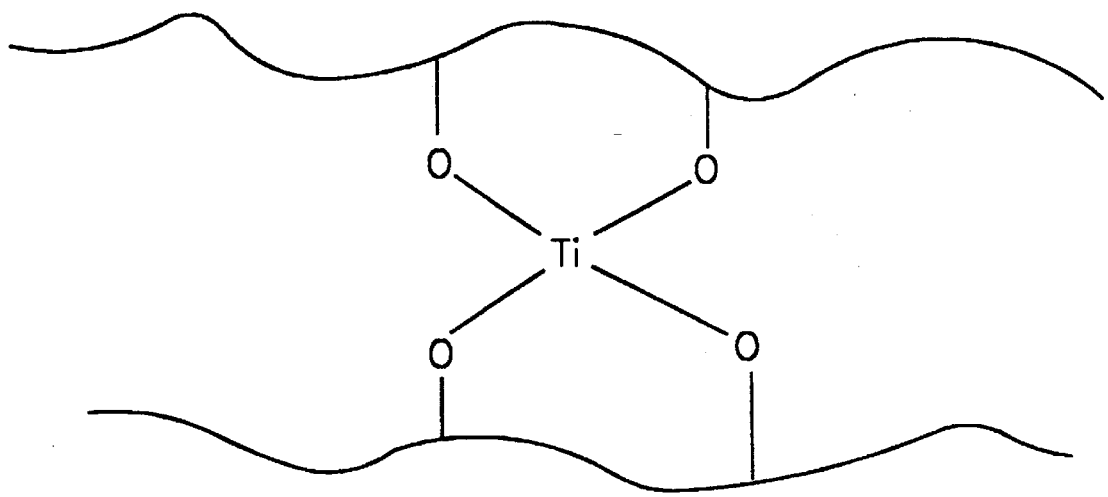
Figure 6:
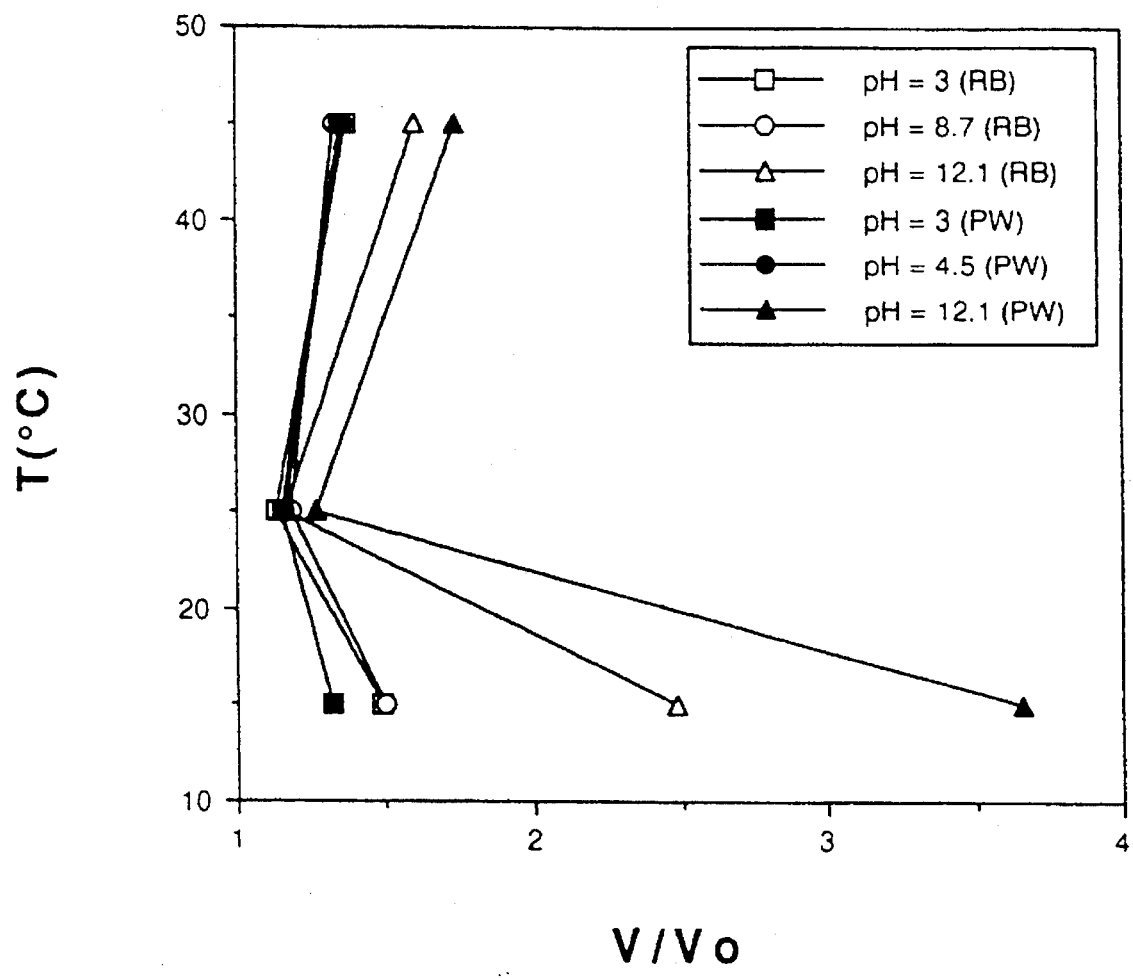
FIG. 6 is a graph of the temperature dependent gel swelling ratio of polyacrylamide in different solutions. Open symbols are ($V/V_o$) in running buffer solution (RB) (0.025M Tris-HCL+ 0.192M glycine+0.1% Sodium dodecylsulfate). Dark symbols are ($V/V_o$) in pure deionized water (PW). Squares are pH 3; circles pH 4.5, and triangles pH 12.1.

In the third method for a reversibly crosslinkable system, crosslinking is achieved by introduction of chelators so that the uncrosslinked polymers (FIG. 5C) are crosslinked by interchain chelation (FIG. 5D). Titanium ion is shown as an example in FIG. 5D.

REVERSIBLY SOLUBILIZABLE POLYMER SYSTEMS

Figure 14:
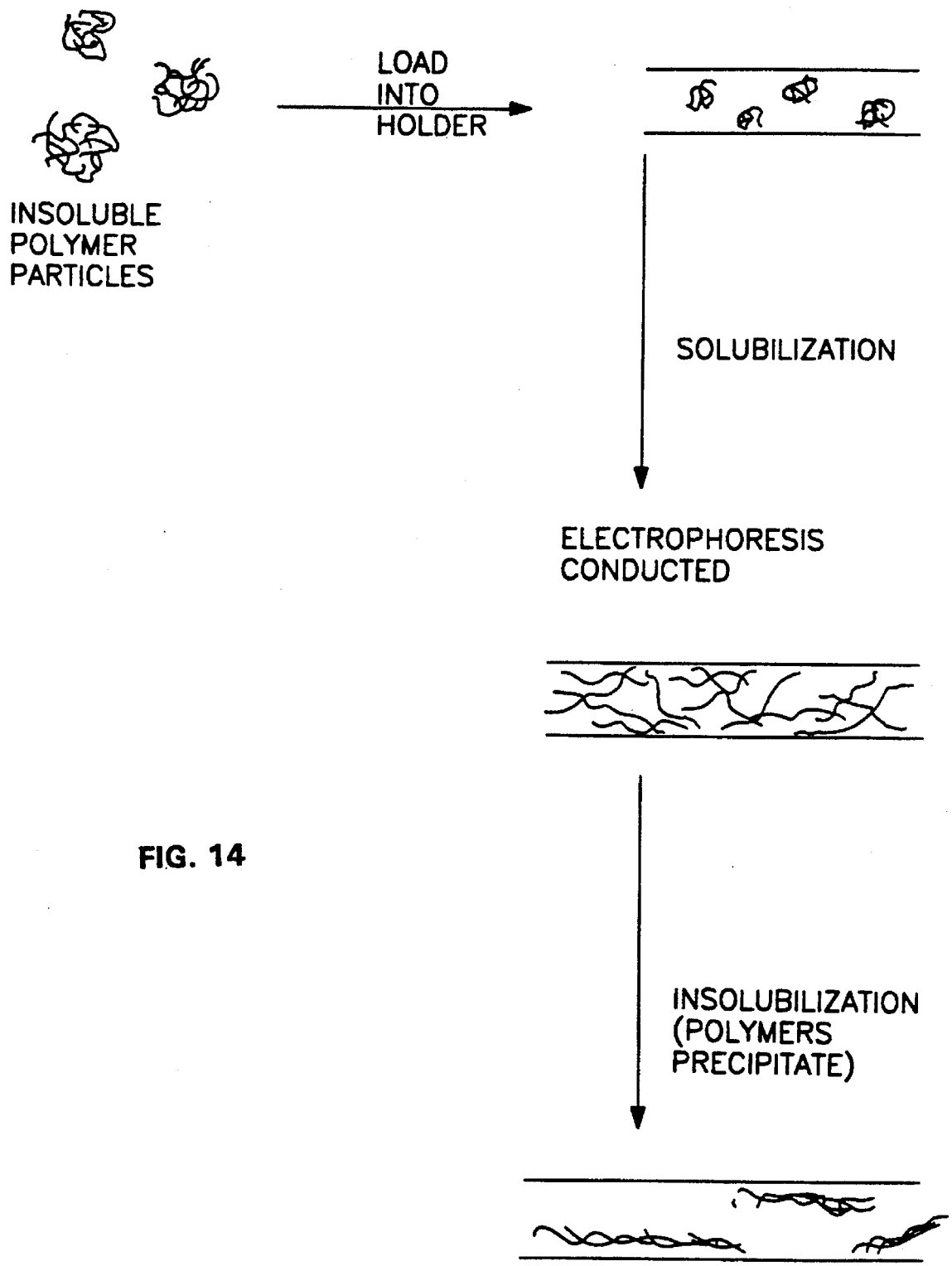
FIG. 14 is a schematic showing a reversibly solubilized system according to the invention.

In the third class of separation media disclosed here, polymer is delivered to a separation channel as an insolubilized dispersion. The insolubilization is achieved by an appropriate selection of solution conditions or composition, which may include temperature, cosolvents, ionic species, pH, or other conditions. After delivery to the separation channel, solution conditions are changed to effect solubilization of the polymer, resulting in an increase in the viscosity of the medium. Electrophoresis is then conducted in this higher viscosity, homogeneous medium. Following electrophoresis solution conditions are changed to render the polymer insolubilized on the medium, at which stage the medium can be flushed or recovered from the separation channel. FIG. 14 illustrates this process in the case where the separation channel is a tube or capillary.

The present invention will be further understood by reference to the following non-limiting examples.

EXAMPLE 1

Preparation of Cross-linked Gel Particles

A. Suspension Polymerization

In inverse emulsion polymerization an aqueous solution of a hydrophilic monomer is dispersed in a continuous hydrophobic oil medium using a surface-active substance which promotes the formation of water-in-oil emulsions. The polymerization is then initiated with either oil-soluble or water-soluble initiators. As far as the end-product of the reaction is concerned, it is clear that inverse lattices are less stratified or flocculate more readily. Continuous and gentle agitation is needed to maintain these lattices as colloidal dispersion indefinitely.

Acrylamide was used as the water soluble monomer and N,N'-methylene-bis-acrylamide as a cross-linker to prepare a $T_{10} C_2$ solution, where $$\%T = \frac{\text{grams of acrylamide} + \text{grams of cross-linker}}{\text{Total volume}} \times 100$$

$$\%C = \frac{\text{grams of cross-linker}}{\text{grams of acrylamide} + \text{grams of crosslinker}} \times 100$$

Sorbitan monostearate (SMS) was used as an emulsifier. The emulsions were formed by dissolving 0.875 g of SMS in 7 ml of o-xylene and adding $T_{10}C_2$ solution (the aqueous monomer solution) with stirring for about 3 to 4 hrs. The temperature is controlled at about 50° C. during polymerization. The crude emulsions are homogenized to decrease the average drop let size and to increase the emulsion stability.

After complete polymerization, the final gel particles can be cleaned by centrifuging several times with deionized water. The gel particles are not monodisperse, however one can filter them to a certain size range, for example, using a 1 µ filter to collect particles less than 1 µ.

B. Precipitation Polymerization

As stated above, precipitation polymerization is carried out above the THCST of the system. The following reagents were combined:

N-isopropylacrylamide: 4.9 g
N,N'-methylene-bis-acrylamide: 0.1 g
Potassium persulfate: 0.2 g
deionized water: 200 ml The system temperature was controlled at about 70° C. The final gel particles are reasonably monodisperse.

EXAMPLE 2

Changing of Gel Swelling Equilibria by Changing Ambient Conditions

The gel swelling equilibria can be changed by changing ambient conditions, i.e. temperature, pH, solvent. Gel disks were prepared by casting in glass tubes (ID= 6.4 mm). The gel disk dimensions were about 6 mm in diameter and about 13 mm in thickness.

After preparing the gel disks, each sample was blotted with laboratory tissue to remove surface water, and weighed. The swelling capacity was determined as the mass ratio of swollen gel to the gel prepared. The volume of the gel as cast (not the dry gel) is denoted by $V_o$.

In each swelling capacity measurement, the diameter and the length of each gel disk was also measured. The properties for acrylamide/N,N'-methylene-bis-acrylamide gels prepared with 10%T and 2% C are shown in FIGS. 4, 7, and 8.

FIG. 4 shows that the volume ratio $(V/V_o)$ of the gel particles can- be decreased with increasing concentrations of ethanol or acetone can be reduced from 1.2–1.4 to 0.2–0.3.

Figure 7:
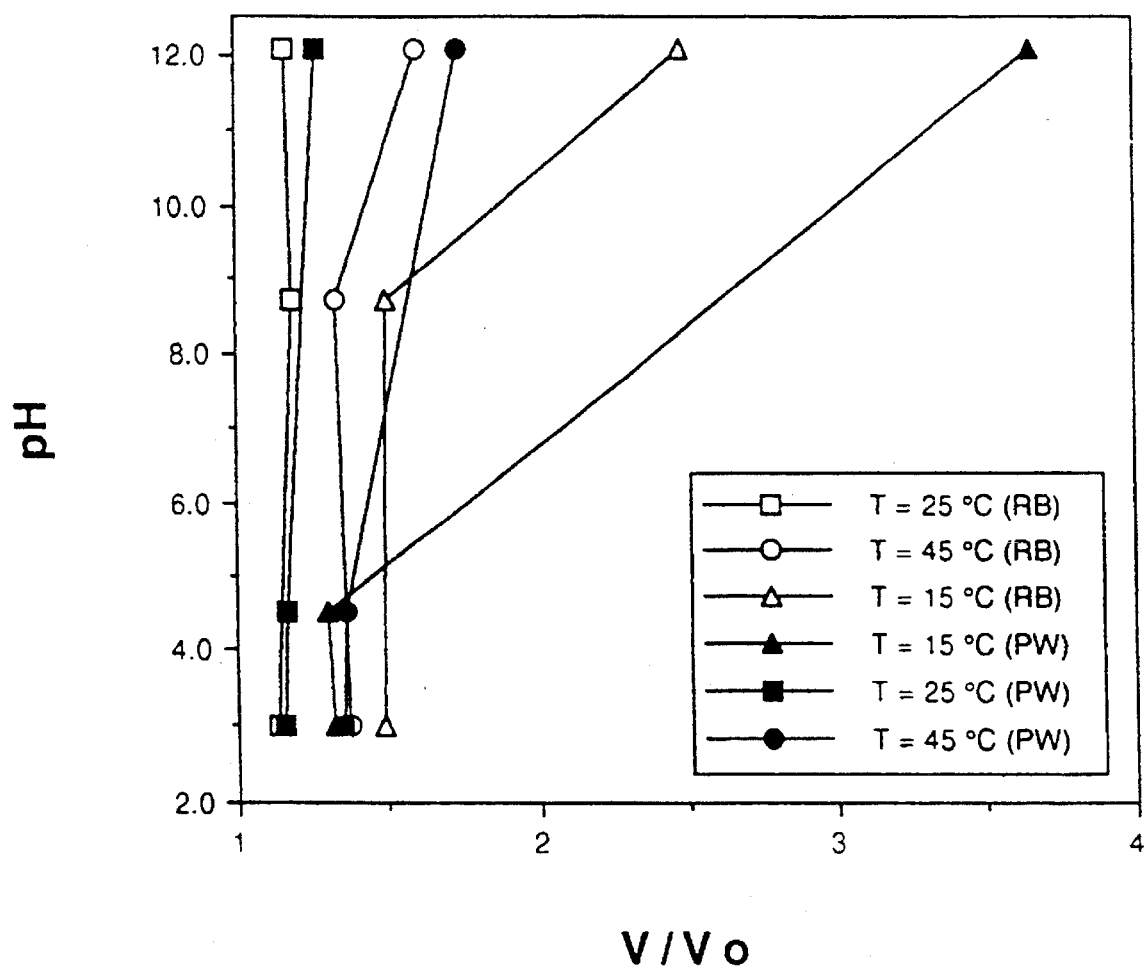
FIG. 7 is a graph of the pH dependent gel swelling ratio of polyacrylamide in different solutions. Open symbols (RB) are ($V/V_o$) in buffer solution (0.025M Tris-HCL+ 0.192M Glycine+ 0.1% Sodium dodecylsulfate), dark symbols (PW) are ($V/V_o$) in deionized water. Squares are 25° C., circles are 45° C., and triangles are 15° C.

FIGS. 7 and 8 show that the volume ratio $(V/V_o)$ can be decreased as a function of pH and temperature.

EXAMPLE 3

Figure 9:
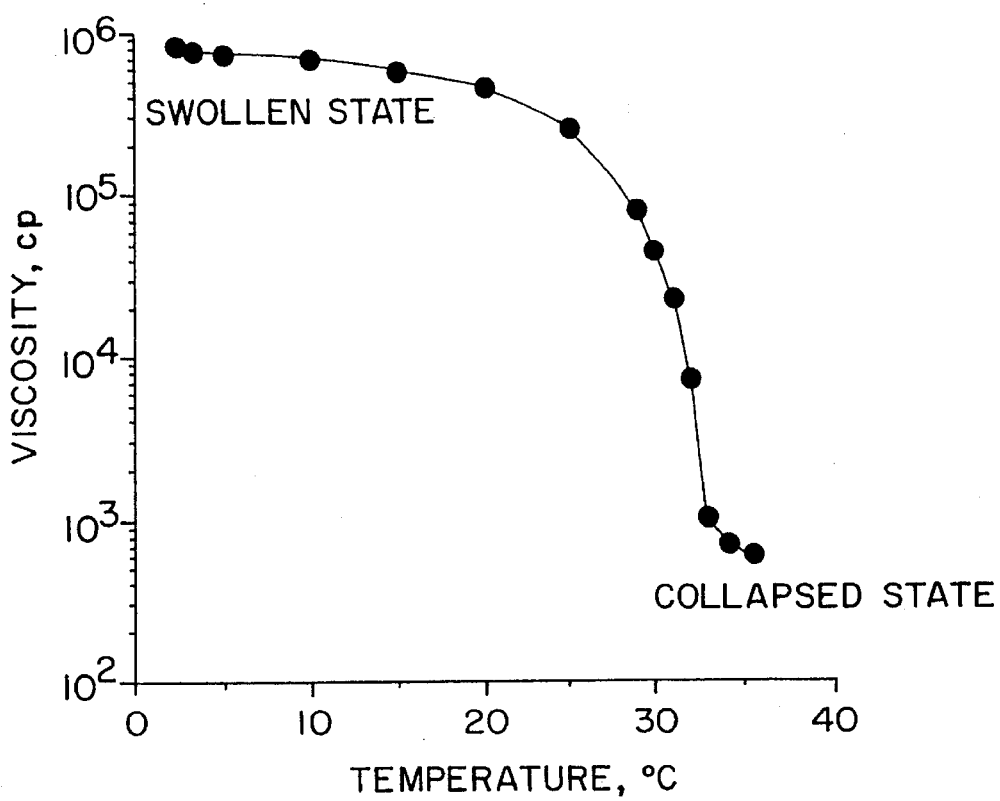
FIG. 9 shows the viscosity of dispersion made according to Example 4 between 4° C. and 35° C.

Suspension Polymerization of Temperature Sensitive Poly(NIPA) Microgels 300 ml toluene and 2.5 g Span 80 were mixed in a round bottom reaction flask equipped with a nitrogen inlet and an overhead stirrer. An aqueous premix of 6.8 g N-isopropylacrylamide, 0.07 g N,N'-methylene bisacrylamide and 0.1 g ammonium persulfate in 50 g water was added to the organic phase while stirring. The mixture was purged with nitrogen for 15 minutes, following which 1.5 ml TEMED was added to initiate polymerization. The reaction was allowed to proceed for 3 hours under nitrogen atmosphere, following which the stirring was stopped, the resulting hydrogel particles settled in the reaction kettle, and the top organic layer was removed. The hydrogel particles were isolated by centrifugation and redispersion in distilled water, repeated three times. FIG. 9 shows a magnified photograph of the resulting microgel dispersion above the LCST (at 35° C.) and below the LCST (at 30° C.).

EXAMPLE 4

Precipitation Polymerization of Temperature-Sensitive Poly(NIPA) Microgels and Viscosity Transition N-isopropylacrylamide (4.9 g) and N,N'-methyl bisacrylamide (0.1 g) were dissolved in 190 g water in a round bottom reaction flask equipped with a condenser, a nitrogen inlet and an overhead stirrer. The solution was purged with nitrogen and the temperature adjusted to 70° C. 10 ml of potassium persulphate solution (containing 0.2 g potassium persulfate were added to initiate polymerization. The reaction was allowed to proceed for 24 hours under nitrogen while stirring.

Figure 10:
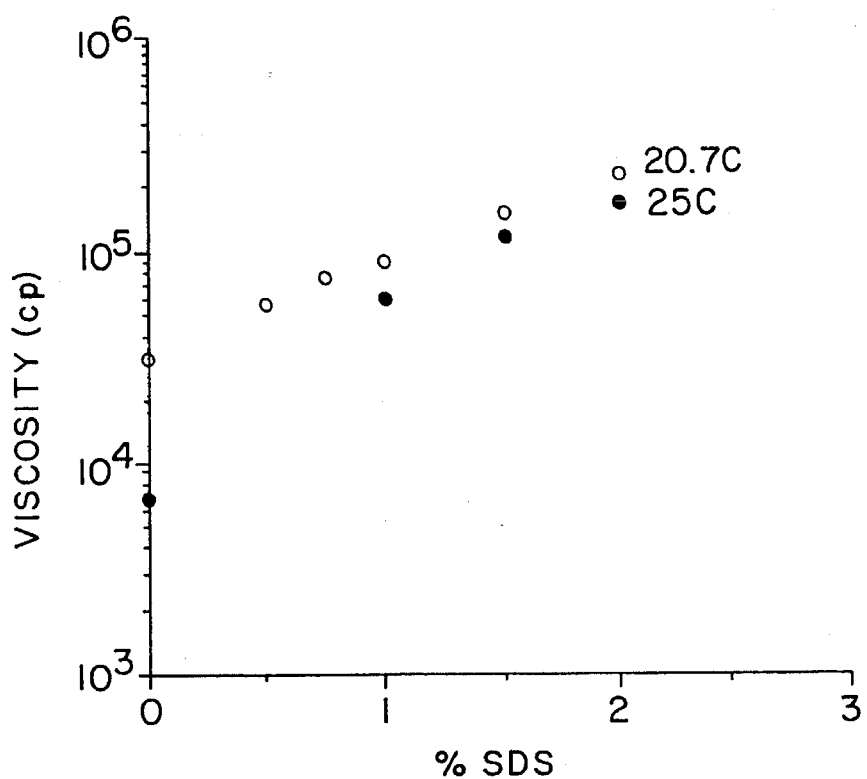
FIG. 10 shows the viscosity of a solution containing SDS according to Example 5.

The resulting hydrogel microspheres were isolated and concentrated by centrifugation, followed by redispersion in distilled water. This centrifugation/redispersion process was repeated three times, and in the final redispersion step the polymer concentration was adjusted was adjusted to 9% by weight of solution. The viscosity of this dispersion was measured between 4° and 35° C., and the resulting data are shown in FIG. 10.

EXAMPLE 5

Viscosity Change Resulting from Surfactant Concentration

Figure 11:
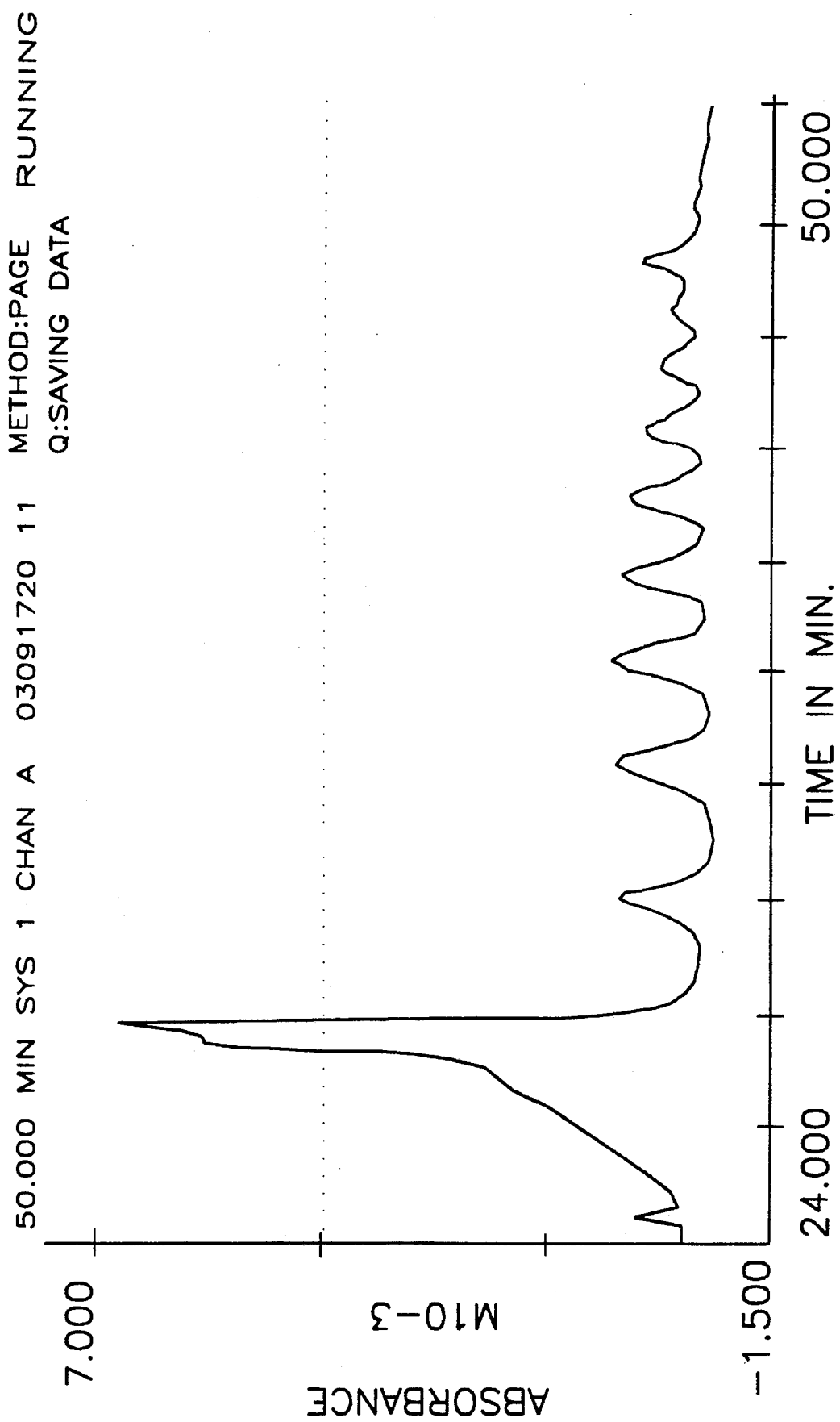
FIG. 11 shows the electropherogram of the analysis shown in Example 7.

Poly(NIPA) microgel solution from Example 4 was adjusted to 8% by weight. Varying amounts of sodium dodecyl sulfate (from 0 to 2 wt %) were added to this solution, and the viscosity of the resulting mixtures were measured. As shown in FIG. 11, the viscosity of the solution containing 2% SDS is approximately 10 times higher than the solution without SDS.

EXAMPLE 6

Suspension Polymerization of Copolymer Microgel System 3.3 ml N,N'-dimethylacrylamide, 3.3 ml N,N'-diethylacrylamide, 0.067 g N,N'-methylene bisacrylamide, 0.1 ammonium persulfate and 7 g Span 80 were dissolved in 45 ml water in a round bottom reaction flask equipped with a nitrogen inlet and an overhead stirrer. While stirring, approximately ⅓ of a total of the 250 ml toluene was added to the aqueous premix creating a thick emulsion. The remaining ⅔ of the 250 ml toluene was added three minutes later. The reaction mixture was purged with nitrogen for 15 minutes, after which 1.5 ml TEMED was added to initiate polymerization. The reaction was allowed to proceed for 3 hours under nitrogen. Approximately 400 ml of acetone was added to the mixture causing phase separation with the hydrogel microspheres precipitating in the lower phase. The upper, organic-rich phase was removed, and distilled water was added to redisperse the concentrated microgels. Residual organics were distilled off in a rotary evaporator.

EXAMPLE 7

Capillary Electrophoresis Separation of dsDNA in Copolymer Microgel System

Figure 12:
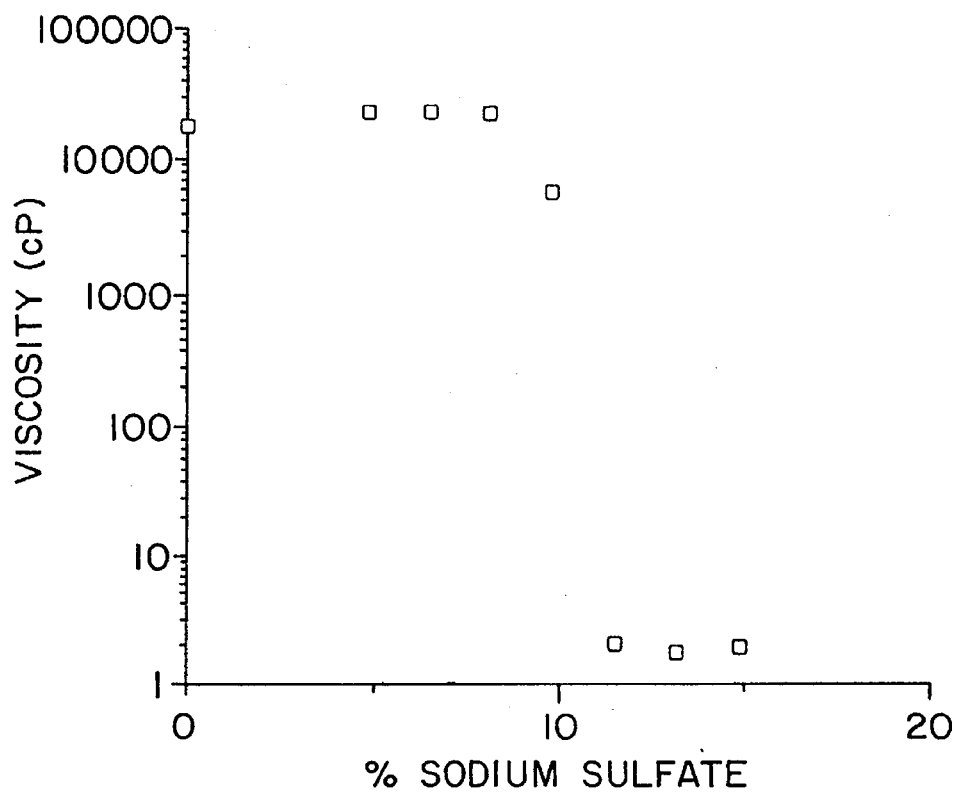
FIG. 12 shows the viscosity versus sodium sulfate concentration in solutions described in Example 9.

An optical window was formed in a fused silica capillary (250 microns ID, 350 microns OD) by burning off the polyimide coating with an electrically heated filament. The capillary was internally coated with linear polyacrylamide by the method of Hjerten (J. Chromatorgr., 347, 191, 1985). Copolymer microgel solution from Example 6 adjusted to 9% polymer by weight in 1X TBE buffer, was loaded into the capillary by heating the gel and capillary to 90° C. and drawing the microgel solution in by vacuum. 27.2 cm of capillary (20.2 cm effective length) was loaded into the cartridge of a Beckman PACE 2100 capillary electrophoresis system. A 10 base pair dsDNA ladder, 0.05 mg/ml, was electrokinetically injected at 4 kV for 15 seconds, cathode at the injector end. After injection, the capillary was run at 2 kV (74 V/cm) with detection by UV at 254 nm. FIG. 12 displays the electropherogram showing resolution of the 10 to 100 base pair peaks.

EXAMPLE 8

Preparation of an Agarose-Microgel Composite Matrix 0.05 g agarose and 10 ml of copolymer microgel from Example 6 (having a polymer concentration of 9%) were mixed and stirred at 80° C. for 15–20 minutes. The solution was then poured into a horizontal electrophoresis unit. After cooling to room temperature for ½ hour, the mixture formed a rigid (non-viscous) gel that could be handled.

EXAMPLE 9

Figure 13:
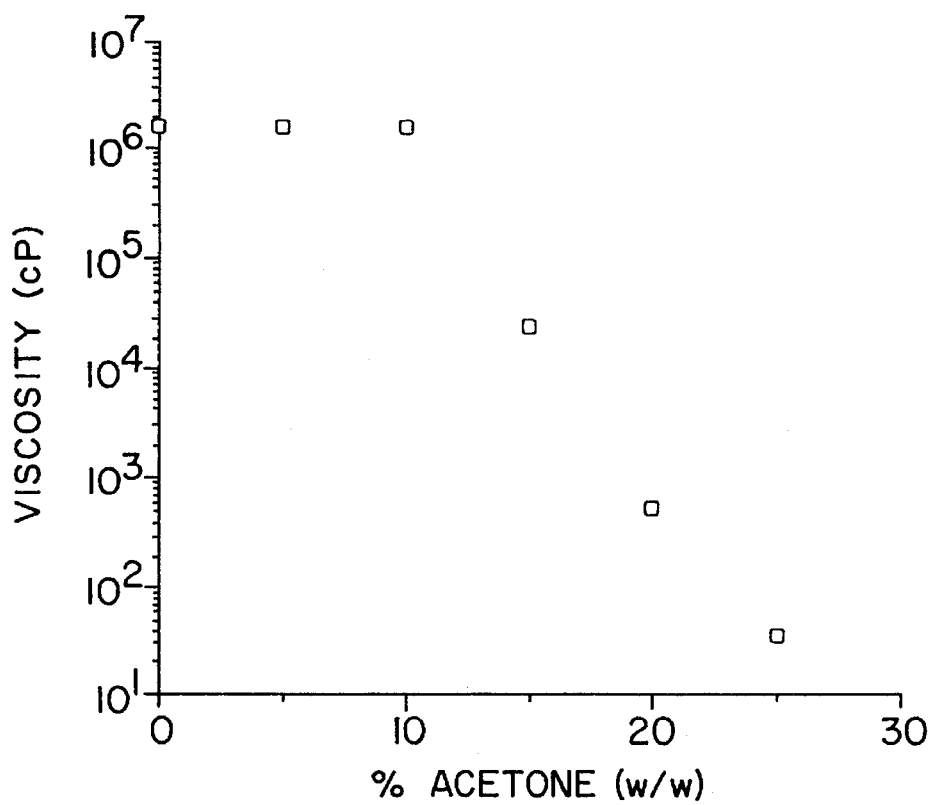
FIG. 13 shows the viscosity varying with acetone concentration of the microgels in described in Example 11.

Chaotropic Switch of Linear, Water Soluble Polymers Suitable for Electrophoresis Aqueous solutions of sodium sulfate were made ranging in concentration from zero to 15 percent by weight. Hydroxyethylcellulose was added to make the solutions 1% by weight polymer. After agitation, the viscosities were measured and are shown in FIG. 13. At sodium sulfate concentrations less than 8%, the solutions were clear and viscous. At concentrations greater than 10%, the solutions were a very low viscosity suspension of the polymer powder.

Polythylene oxide (MW 900,000) was dispersed similarly at 4% by weight in solutions of varying sodium sulfate concentration. At concentrations above 7%, the polymer coagulated into a solid phase. Below this, the solutions were clear and viscous. Both polymers, when made into small microgel particles, will exhibit a viscosity switch due to varying the concentration of a chaotropic agent such as sodium sulfate.

EXAMPLE 10

Reversible Crosslinking of a Derivatized Cellulose with a Titanium Chelate

A stock solution of 0.5% (w/w) of a cis-diol derivatized hydroxyethylcellulose solution was prepared and the viscosity measured as shown in Table 1. 18 ml of this solution was acidified with 200 mg of glacial acetic acid and 100 mg of triethanolamine titanate chelate was added with vigorous shaking. The system gelled in seconds and the viscosity was measured. 300 mg of concentrated sulfuric acid was added and mixed into the gel with a spatula following by continued mixing on a rocking stage. After 30 minutes the viscosity was measured again.

TABLE 1

| Reversible Viscosity Switch of Derivatized Cellulose with Titanium Chelate | |
|---|---|
| | Viscosity (cP) |
| Original solution | 394 |
| After addition of chelate | 444000 |
| After addition of sulfuric acid | 232 |

This example system can be loaded at low viscosity, the titanate added and the system gelled for electrophoresis. After use, the system can be lowered in viscosity by acid and removed.

EXAMPLE 11

Solvent Switch of Polyacrylamide Microgels in an Acetone/Water System

A range of acetone/water blends were prepared. Polyacrylamide microgel powder (45–90 microns diameter fully hydrated) was added to each to make 7% by weight solutions. After agitation for several hours, the solution viscosities were measured. As shown in FIG. 14, in pure water the viscosity was at least 1.5 million cP, while at 25% acetone by weight the viscosity had dropped to 36 cP.

Modifications and variations of the method of the present invention will be obvious to those skilled in the art from the foregoing detailed description. Such modifications and variations are intended to come within the scope of the following claims.

We claim:

1. In an electrophoretic device comprising an electrophoretic medium, the improvement which comprises:

an electrophoretic medium comprising a dispersion of particulate chemically-crosslinked microgels having particle sizes with a distribution of particles no smaller than about 10 nm and no larger than about 2 mm, wherein the weight concentration of said microgels in said dispersion is between about 1% and 50% and wherein said medium is reversibly convertible between a pumpable low viscosity state and an electrophoretically sieving high viscosity state, said high viscosity state characterized by a viscosity of at least 100% greater than the viscosity of said medium in said low viscosity state, and wherein the conversion of said low viscosity state to said high viscosity state can be affected by a change in temperature, pH, solvent concentration, ionic strength, presence and concentration of a specific ion, or other property or combinations of properties of said medium.

2. A device according to claim 1 wherein said conversion from said low viscosity state to said high viscosity state is driven by a change in the volumes of said particles by at least about 50%.

3. A device according to claim 1 or 2 wherein said solution further comprises ionic surfactants.

4. A device according to claim 1 or 2 wherein said solution further comprises nonionic surfactants.

5. A device according to claim 1 or 2 wherein said solution further comprises water-soluble polymers.

6. A device according to claim 1 or 2 wherein said medium comprises a granular bed of said particles in said high viscosity state and said particles are molecular sieves.

7. A device according to claim 1 or 2 wherein said medium further comprises agarose.

8. A device according to claim 1 or 2 wherein the conversion between said high- and low-viscosity states are achieved by a change in temperature, which changes the pore size or physical structure of said microgel.

9. A device according to claim 1 or 2 wherein said microgels comprise a plurality of different microgels formed from the same monomers, but at a different concentration, from different monomers at the same concentration or a different concentration, and/or having degrees of crosslinking.

10. In an electrophoretic device comprising an electrophoretic medium, the improvement which comprises:

an electrophoretic medium comprising polymer chains having hydrophobic and hydrophilic moieties, wherein said medium is reversibly convertible between an electrophoretically sieving high viscosity state and a pumpable low viscosity state, said high viscosity state characterized by a viscosity of at least 100% greater than the viscosity of said medium in said low viscosity state, and wherein the conversion of said low viscosity state to said high viscosity state can be affected by a change in temperature, pH, solvent concentration, ionic strength, presence and concentration of a specific ion, or other property or combinations of properties of said medium which cause coalescence of said hydrophobic or hydrophilic groups on contiguous polymeric chains to form effective crosslinks of chains in said medium.

11. In an electrophoretic device comprising an electrophoretic medium, the improvement which comprises:

an electrophoretic medium comprising polymer chains having ionic moieties and counter-ions, wherein said medium is reversibly convertible between an electrophoretically sieving high viscosity state and a pumpable low viscosity state, said high viscosity state characterized as having a viscosity of at least 100% greater as compared to the viscosity of said medium in said low viscosity state, and wherein the conversion of said low viscosity state to said high viscosity state is affected by exchange of said counter-ions with counter-ions of higher valency whereby ionic moieties on contiguous polymeric chains associate with said counter-ions of higher valency to form effective crosslinks of chains in said medium.

12. In an electrophoretic device comprising an electrophoretic medium, the improvement which comprises:

an electrophoretic medium comprising polymer chains having chelatable ligand, wherein said medium is reversibly convertible between an electrophoretically sieving high viscosity state and a pumpable low viscosity state, said high viscosity state characterized as having a viscosity of at least 100% greater as compared to the viscosity of said medium in said low viscosity state, and wherein the conversion of said low viscosity state to said high viscosity state is affected by addition of a chelating agent whereby chelatable ligands on contiguous polymeric chains associate with said chelating agent to form effective crosslinks of chains in said medium.

13. The device of any of claims 1, 10, 11 or 12 selected from the group consisting of capillaries for gel electrophoresis, tube and slab gel holders.

14. A process of filling and flushing the electrophoretic medium of an electrophoretic device comprising the steps of providing an electrophoretic device according to any of claims 1, 2, 10, 11, or 12;

and changing a condition of said medium selected from the group consisting of temperature, pH, solvent concentration, ionic strength, presence or concentration or a specific ion or other property or combination of properties of said medium to affect the conversion between a high viscosity state and a low viscosity state.

15. The process according to claim 14 further comprising the steps of conducting an electrophoretic separation of components of a sample on said medium, changing one or more of said conditions of said medium, and conducting further electrophoretic separation of said components on said medium.

16. The process according to claim 14 further comprising the steps of adding a sample to said medium;

conducting an electrophoretic separation of components of said sample;

recovering a separated component of said sample from said medium by excision of a portion of said medium and deswelling said excised portion.

17. The process of claim 14 further comprising the step of analyzing a sample on said electrophoretic device.

18. The process of claim 17 further comprising the step of removing said medium from said device and subjecting said medium to additional analytical processing.

19. The process according to claim 18 wherein said analytical processing comprises staining said medium and determining the location of components of said sample.

20. The process of claim 14 wherein said electrophoretic device is selected from the group consisting of capillaries for gel electrophoresis, tube gel and slab gel holders.

21. In an electrophoretic device comprising an electrophoretic medium, the improvement which comprises:

said electrophoretic medium comprising a composition reversibly convertible going from a first pumpable state to a second continuous electrophoretic gel state, wherein in said first pumpable state said composition is discrete particles of a cross-linked N-substituted polyacrylamide of a size in the range of 10 nm to 2 mm in an aqueous medium; and in said second state said particles are swollen and form a continuous gel, wherein said change from one state to another state occurs with a change in temperature.

22. An electrophoretic device according to claim 21, wherein said N-substituted polyacrylamide is N-isopropyl polyacrylamide.

23. An electrophoretic device according to claim 22, wherein said device comprises a capillary of a diameter in the range of 50 μ to 250 μ and said particles are smaller than said diameter.

24. In an electrophoretic device comprising an electrophoretic medium, the improvement which comprises:

an electrophoretic medium comprising a dispersion of a particulate chemically-crosslinked microgel having particle sizes with a distribution of particles no smaller than about 10 nm and no larger than about 2 mm, wherein the weight concentration of said microgel in said dispersion is between about 1% and 50%, agarose, and wherein said medium is reversibly convertible between a pumpable low viscosity state and an electrophoretically sieving gel slab state, and wherein the conversion of said low viscosity state to said gel slab state occurs with a change in temperature.

* * * * *